(12) United States Patent
Pevere et al.

(10) Patent No.: US 6,297,398 B1
(45) Date of Patent: *Oct. 2, 2001

(54) METHOD FOR THE SYNTHESIS OF PERFLUOROSULPHONAMIDES, PERFLUOROSULPHONAMIDES AND THEIR SALTS, AND A SULPHONATION REAGENT

(75) Inventors: Virginie Pevere, Lyons; Emmanuel Marx, Chatillon d'Azergues; Laurent Gilbert, Lyons, all of (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/423,486
(22) PCT Filed: May 15, 1998
(86) PCT No.: PCT/FR98/00973
§ 371 Date: Nov. 9, 1999
§ 102(e) Date: Nov. 9, 1999
(87) PCT Pub. No.: WO98/52886
PCT Pub. Date: Nov. 26, 1998

(30) Foreign Application Priority Data

May 16, 1997 (FR) .................................................. 97 06064

(51) Int. Cl.$^7$ ................................................. C07C 303/18
(52) U.S. Cl. ................................. 564/82; 560/12; 564/86; 564/96; 564/97
(58) Field of Search .............................. 560/12; 564/82, 564/86, 96

(56) References Cited

U.S. PATENT DOCUMENTS 5,874,616 * 2/1999 Howells et al. ........................ 564/82

FOREIGN PATENT DOCUMENTS

| 2 724 380 | 3/1996 | (FR) | ............................ C07C/311/48 |
| WO 90/11999 | 10/1990 | (WO) | ............................ C07C/311/48 |
| WO 97/23448 | 7/1997 | (WO) | ............................ C07C/303/38 |

OTHER PUBLICATIONS

Burdon et al., 'Fluorinated Sulfonic Acids, etc.' Journal of the Chemical Society, No. 6, pp. 2574–2578, Jun. 1957.*

L.M. Yagupol'Skii, et al.: "Trifluoromethylsulphonylimino and bis (trifluoromethylsulphonylimino) derivatives of arenesulphonic acids" Russian Journal of Organic Chemistry, vol. 31, No. 5, May 1995, pp. 691–695, XP002051637.

D.D. Desmarteau et al.: "N–Fluoro–bis(trifluoromethanesulphyl) imide. An improved synthesis" Journal of Fluorine Chemistry, vol. 52, No. 1, Apr. 1991, pp. 7–12, XP002025807, Lausanne, CH (See entire document).

B. Heleferich et al.: "Bis–'alkylsulfonsaure!–imide", Berichte Der Deutschen Chemischen Gesellschaft, vol. 75, 1942, pp. 532–536, XP002025808 Weinheim, DE. (See entire document).

International Search Report.

* cited by examiner

Primary Examiner—Peter O'Sullivan
(74) Attorney, Agent, or Firm—Jean-Louis Seugnet

(57) ABSTRACT

The invention concerns a method of sulphonation characterised in that it consists in contacting a nucleophile whose nucleophilic atom is a nitrogen atom with a reagent comprising by successive or simultaneous addition: a heavy sulphonyl halide (i.e. whose atomic number is not less than that of chlorine), advantageously suphonyl chloride; and an organic base both not capable of alkylation and lipid soluble; and the organic part of said sulphonyl is perfluorinated on the carbon carried by the sulphur. The invention is applicable to organic synthesis.

25 Claims, No Drawings ically relates to a reaction for the sulpho-
METHOD FOR THE SYNTHESIS OF PERFLUOROSULPHONAMIDES, PERFLUOROSULPHONAMIDES AND THEIR SALTS, AND A SULPHONATION REAGENT This application is an application under 35 U.S.C. Section 371 of International Application Number PCT/FR98/00973, filed on May 15, 1998.

The subject-matter of the present invention is a process for the synthesis of perfluorosulphonamides and of perfluorosulphonimides. The latter can be obtained in the form of their salts. The present invention is also targeted at a perfluorosulphonylation reagent.

It more particularly relates to a reaction for the sulphonylation of a nitrogenous functional group carrying an electron-withdrawing radical. It is also particularly targeted at the sulphonation of a sulphonamide, in particular a fluorinated sulphonamide. The synthesis of sulphamides is in particular targeted at the case where the sulphamide is prepared with the aim of a subsequent sulphonation (in a second stage, in the same reactor, or simultaneously in situ).

Fluorinated sulphonimide derivatives are increasingly being developed for electrical applications and in particular for forming batteries and for their catalytic power. The most frequently used compound derived from these sulphonimides is the lithium derivative, that is to say the salt of this imide, an imide which is itself very acidic.

The synthesis of these sulphonimides has already been carried out but employs processes which are particularly problematic and difficult to use.

The inserted Application WO 97/23.448 describes a process which, like all those which have preceded it (cf. FR-A-2,724,380), uses perfluoroalkanesulphonyl fluorides, the reactivity of which is very specific and the by-product of which is the fluoride ion, which requires the use of equipment which is resistant thereto and thus expensive, as well as exhaustive removal before discharge of the effluents. The very high volatility and the operating conditions result, in the commonest cases, in the operation being carried out under relatively high pressures. To cap it all, the sensitivity to water of perfluoroalkanesulphonyl fluorides seems, in the light of this document, particularly high.

A few trials have been carried out on sulphonyl halides but have resulted in failures (for the problems relating to these syntheses, see Application WO 90/11.999, in particular page two, lines 30 to 35 et passim). This is in particular the case with bistrifluoromethylsulphinimide, which seems particularly difficult to prepare from trifluoromethanesulphonyl chloride. This is why one of the aims of the present invention is to provide a process which makes it possible to obtain fluorinated imides of the above type by using heavy sulphonyl halides (that is to say, halides corresponding to a halogen with an atomic number at least equal to that of chlorine).

It is preferable, for economic reasons, to use sulphonyl chlorides. This aim and others which will become apparent subsequently are achieved by means of a synthetic process which comprises a stage in which a nucleophile, the nucleophilic atom of which is a nitrogen, is brought into contact with a reactant comprising, for successive or simultaneous addition: a sulphonyl heavy halide (that is to say, in which the atomic number of the halogen is at least equal to that of chlorine), advantageously sulphonyl chloride; and an organic base which simultaneously cannot be alkylated and is liposoluble;

and with the condition that, when the nitrogen, the nucleophilic atom of the substrate, does not carry a sulphonyl functional group for which the carbon adjoining the sulphur is perfluorinated, the organic part of the said sulphonyl heavy halide is perfluorinated on the carbon carried by the sulphur. However, in all cases, the process is particularly advantageous when the organic part of the said sulphonyl heavy halide is chosen so that it is perfluorinated on the carbon carried by the sulphur.

Thus, the present invention provides a process for the synthesis of perfluorosulphonamides and of sulphonimides which exhibits at least one, advantageously two, sulphonyl group for which the carbon adjoining the sulphur is perfluorinated.

The salts of these imides are prepared from these imides in a way known per se. The process according to the present invention can comprise a stage of preparation of these salts (as in the examples).

The notion of organic base which simultaneously cannot be alkylated and is liposoluble is explained subsequently.

The said nitrogen of the nucleophilic functional group advantageously carries a hydrogen or a negative charge (anion).

It is preferable for the said nitrogen of the nucleophilic functional group to carry two hydrogens (and even 3 in the specific case of ammonia or aqueous ammonia, which makes it possible to synthesize the preferred category of substrates, namely sulphamides, advantageously perfluorinated on the carbon adjoining the sulphur, preferably corresponding to the definition of Rf) or else to carry one hydrogen and one negative charge (anion).

In particular, the nucleophile can be a sulphonamide (sulphamide), in particular in the form of a salt, advantageously of an organic base which cannot be alkylated. The process is suitable in particular even when the organic part of the said sulphonamide (sulphamide) is perfluorinated on the carbon carried by the sulphur.

Conventional sulphamides (corresponding to non-perfluorinated sulphonic acids, such as Ar—$SO_3H$, with Ar representing an aryl, and $RSO_3H$, with R representing an alkyl) does not warrant being in the salt form, a salt which would furthermore be difficult to obtain with the preferred bases of the invention. In the present description, ALK-yl is taken in its etymological sense of hydrocarbon-comprising residue of an ALK-ohol, with the alcohol (or ohol) functional group being ignored.

The nucleophilic substrate thus exhibits, as nucleophilic functional group, a functional group advantageously chosen from sulphamides of sulphonic acids in which the sulphur is bonded to an aryl or an aliphatic residue, including alkyls, preferably to an aliphatic residue which are perfluorinated on the carbon adjoining the sulphur. In general, the carbon number of the nucleophilic substrate varies from 1 to 15 and even from 1 to 10.

Thus, from the above and from the study which has led to the present invention, it is evident that the nucleophiles (in the neutral form or especially in the anion form) for which the problems, because they are difficult, are particularly well solved by the present invention are those for which the associated acid exhibits a pKa at most equal to approximately 7, advantageously to 6, preferably to 5.

Ammonia constitutes a case apart and can, in the case of ammonia, result in an imide by two successive in situ condensations.

The condensation of the sulphonyl heavy halides targeted by the present invention with ammonia or aqueous ammonia can constitute a stage prior to the condensation of the amides.

In the present description, the term "approximately" is employed to underline the fact that the values which follow it have been rounded off mathematically and in particular that when the figure or figures furthest to the right of a number are zeros, these zeros are positional zeros and not significant figures, except, of course, when otherwise specified.

The said organic base which cannot be alkylated is advantageously chosen from hindered dialkylphosphines, trialkylphosphines, phosphonium hydroxides, hindered dialkylamines, trialkylamines or ammonium hydroxides. It is also possible to envisage phosphorus-comprising and nitrogen-comprising rings exhibiting an appropriate basicity (see infra). For example nuclei of the pyridine type, but, according to the present invention and in contrast to standard techniques, these basic functional groups of aromatic heterocycles do not constitute the preferred bases.

It is desirable for the said base which simultaneously cannot be alkylated and is liposoluble to be chosen from hindered dialkylphosphines, trialkylphosphines, phosphonium hydroxides, hindered dialkylamines, trialkylamines or ammonium hydroxides.

It is recommended that the said base which simultaneously cannot be alkylated and is liposoluble should exhibit at least a significant (symbol "s" in the Handbook of Chemistry and Physics) solubility in benzene, advantageously a high (symbol "v" in the Handbook of Chemistry and Physics) solubility in benzene.

It is recommended that the substrate should exhibit at least a significant (symbol "s" in the Handbook of Chemistry and Physics) solubility in benzene, advantageously a high (symbol "v" in the Handbook of Chemistry and Physics) solubility in benzene.

Likewise, according to the present invention, it is preferable to see to it that the nucleophilic substrate is in the form of a salt of an organic base which cannot be alkylated, this optional saline compound between the organic base and the said substrate (when it is acidic, as in the case of perfluorosulphonamide) exhibits at least a significant (symbol "s" in the Handbook of Chemistry and Physics) solubility in benzene, advantageously a high (symbol "v" in the Handbook of Chemistry and Physics) solubility in benzene.

In the preceding cases, it is, of course, particularly satisfactory for the solubility to be such that the benzene and the bases targeted above are miscible in all proportions (symbol "∞" in the Handbook of Chemistry and Physics).

In choosing the base, it is advisable to observe basicity restrictions, thus, it is desirable for the $pK_a$ of the acid associated with the said organic base (forming the optional salt with the nucleophile) to be greater than or in the region of that of the said nucleophile [for example sulphonamide (which in principle carries two hydrogens on the nitrogen)].

Likewise, it is also desirable for the $pK_a$ of the acid associated with the said base which cannot be alkylated and is liposoluble to be equal to and preferably greater than that of the said sulphonamide.

When they are not the same, it is desirable for the difference between the $pK_a$ values of the associated acids and that of the said nucleophile (to be at least equal to 1, advantageously to 2, preferably to 3.

Although this is not preferred, the bases can be mixtures of bases, provided which the mixture meets the restrictions and, even preference, specified hereinabove.

It can be specified that, when the said nucleophile is sulphamide, for reasons of ease of handling, it is preferable for the said organic base which cannot be alkylated and the said base which simultaneously cannot be alkylated and is liposoluble to be identical. The reaction can be carried out without solvent, in particular when the organic bases are chosen from the preferred ones, that is to say particularly liposoluble and not very polar bases (for example and in particular, trialkylamines with a carbon number greater than 6; trialkylamines with a carbon number of less than 7 but exhibiting at least one secondary or tertiary radical, advantageously two, or hindered dialkylamine).

As regards an advantageous implementation of the said stage, the operation of bringing into contact is carried out in an organic solvent, advantageously of low [lacuna] advantageously at most 5% by mass, preferably at most 2% by mass).

The reaction temperature is advantageously at least equal to the finishing melting point (apart from insolubles and in particular salts [hydrohalide, and the like]) of the reaction mixture and advantageously at most 100° C. (advantageously two significant figures, preferably 3), advantageously to a temperature at most equal to approximately 50° C., preferably to 40° C. and advantageously at least equal to 0. Thus, the reaction temperature is advantageously situated within the closed range defined by the finishing melting point and 100° C. Preferably within the range 0° C. and 50° C., more preferably within the range 0 and 40° C. Although the reaction can be carried out under a different pressure, it is easier to carry it out at atmospheric pressure. In this case, it may be opportune to choose solvents so that there is a possible reflux at a temperature chosen within the above temperature ranges.

In order to obtain good kinetics of reaction, it is recommended to carry out the said operation of bringing into contact in an organic solvent which is chosen so that, when the said nucleophile is sulphamide salt, the said salt is soluble therein, advantageously to a concentration level of at least 0.05M, preferably of at least 0.2M.

To obtain the above solubilities, it is also possible to vary the said organic base which cannot be alkylated. It is also possible to vary the solvent and the organic base simultaneously.

The bases employed in the present invention advantageously exhibit from 3 to approximately 40 carbon atoms, preferably from 6 to approximately 30 carbon atoms, more preferably from 8 to 25 carbon atoms. In particular, when the carbon number is low (that is to say less than 7), it is preferable for at least one of the substituents of the basic atom to be at least secondary. These bases are, for economic reasons, advantageously amines.

The bases can also be polyfunctional bases (for example, substituted ethylenediamines and in particular tetramethylethylenediamine), in which case the above restriction must be reduced to the number of useful basic functional groups.

The most useful solvents are solvents of relatively low polarity, of the chlorine solvent or aromatic solvent type, provided that, preferably, the said optional salt is sufficiently soluble therein.

The said solvent of low polarity, which, it should be remembered, can be a mixture, is advantageously chosen from those for which the polarity ($E^f_T$, expressed in kcal per mol) is at most equal to 40 (advantageously two significant figures). However, for reasons of industrial hygiene and of environmental protection [some are already banned], non-aromatic chlorinated derivatives, in particular aliphatic chlorinated derivatives (such as methylene chloride or chloroform) or alkenic chlorinated derivatives (for example trichloroethylene), are generally to be avoided as solvent. Furthermore, although giving good results, they do not constitute the family with the best performance (thus, the solubility in water of methylene chloride is of the order [lacuna] 2% by volume, i.e. 2.6% by mass).

Taking into account the above, the said solvent of low polarity is advantageously chosen from oxygen-comprising organic compounds (in particular ethers, esters, even ketones), hydrocarbons (including petroleum fractions) or ring-halogenated aromatic hydrocarbons.

Preferably, the said solvent of low polarity can advantageously be chosen from substituted benzenes and ring-halogenated [lacuna] hydrocarbons.

Respecting the stoichiometry of the reaction is desirable as regards the sulphonyl halide and the sulphonamide (sulphamide). A tolerance of plus or minus 20% is entirely acceptable and depends essentially on the respective cost of the reactants.

As regards the amount of the said base which cannot be alkylated and is liposoluble introduced during the reaction, it is at least equal to the amount necessary to neutralize the hydrohalic acid given off.

When the nitrogen of the substrate carries two hydrogens (three in the very particular case of ammonia, which makes it possible to synthesize, in particular in situ, the preferred category of substrates, namely sulphamides, advantageously perfluorinated on the carbon adjoining the sulphur, preferably corresponding to the definition of Rf; of course, in the case of an in situ synthesis, it is necessary to take into account the sulphonylation reaction of ammonia) and when the nucleophile is not in the salt form, it can be advantageous to bring the amount of base(s) introduced during the reaction to a value at least equal to twice the amount necessary to neutralize the hydrohalic acid given off.

In other words and more specifically, it is preferable for the sum of the bases (base of the substrate salt [see supra] and liposoluble organic base which cannot be alkylated) to be at least equal to the sum of the acidity given off in the form of hydrohalic acid and of the acidity of the sulphone compounds (in particular sulphonimides) being formed.

Thus, taking into account the above, it is desirable for the total amount of base(s) to be at least equal to one times [lacuna] amount stoichiometrically necessary to neutralize the hydrohalic acid given off, advantageously at least equal to the sum of the acidity given off in the form of hydrohalic acid and of the acidity of the sulphone compounds (in particular sulphonimides); more specifically, it is recommended to use an amount of base (expressed, of course, as equivalent) at least equal to the sum of the acidity of the sulphone compounds and of one and a quarter times the amount stoichiometrically necessary to neutralize the hydrohalic acid given off, advantageously at least equal to the sum of one and a half times the acidity given off in the form of hydrohalic acid and of the acidity of the sulphone compounds.

It is also preferable to avoid an excessively large excess of base(s); this is why it is desirable for the sum of the bases (base of the substrate salt [see supra] and liposoluble organic base which cannot be alkylated) to exhibit an excess, with respect to the sum of the acidity given off in the form of hydrohalic acid and of the acidity of the sulphone compounds being formed, at most equal to 3 times, advantageously to two times, preferably to one times the amount of hydrohalic acid given off.

The process with respect to the present invention is particularly advantageous for the synthesis of compounds obtained from sulphonyl chloride in which the organic part is perfluorinated (that is to say, corresponds to $CX_2$, see infra) on the carbon carried by the sulphur.

The present invention is targeted in particular at the case where the organic part of the said sulphonyl chloride is the same as that of the said sulphonamide.

The present invention is also targeted at the case where the organic part of the said sulphonyl chloride carries, at least transiently in the form of a reaction intermediate, the sulphonamide functional group. Which makes it possible to prepare cyclic products or polymeric products. As is well known generally to a person skilled in the art for condensation reactions, cyclization or polycondensation takes place according to the number of chain members separating the two functional groups and according to the dilution of the reaction mixture (this well known phenomenon is recalled, inter alia, in the inserted application WO 97/23448).

The present invention is particularly useful for carrying out the condensation of the present invention when the organic parts, which are alike or different, of the said sulphonyl chloride and of the said sulphonamide are chosen from radicals of formula (Rf):

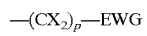

where:
the X groups, which are alike or different, represent a fluorine or a radical of formula $C_nF_{2n+1}$, with n an integer at most equal to 5, preferably to 2;
p represents an integer at most equal to 2;
EWG represents an electron-withdrawing group, the possible functional groups of which are inert under the reaction conditions, advantageously fluorine or a perfluorinated residue of formula $C_nF_{2n+1}$, with n an integer at most equal to 8, advantageously to 5.

The total carbon number of Rf is advantageously between 1 and 15, preferably between 1 and 10.

EWG can be or carry a sulphonyl heavy halide functional group. Which makes it possible to prepare, in situ, compounds carrying both the nucleophilic functional group and the sulphonyl heavy halide functional group, compounds where the organic part of the said sulphonyl chloride carries the sulphonamide functional group. Which makes it possible to prepare cyclic products or polymeric products.

As was indicated above, the most advantageous compounds obtained from the imides synthesized according to the present invention are lithium derivatives, the said process advantageously comprises, after an optional purification and/or isolation stage, a stage of treatment with lithium hydroxide or a basic lithium salt.

According to the present invention, the starting sulphonamides can advantageously be synthesized by the action of the same sulphonyl halide as that used for the synthesis of the imide. This synthesis can be carried out in protic or aprotic polar solvents, provided that they have no tendency to be alkylated. In particular, the reaction can be carried out in symmetrical or unsymmetrical, cyclic or non-cyclic ethers.

Another aim of the present invention is to provide a reactant which is useful in the processes of the above type.

This aim, and others which will become apparent subsequently, is achieved by means of a reactant which comprises, for successive or simultaneous addition:
a sulphonyl heavy halide (that is to say, in which the atomic number of the halogen is at least equal to that of chlorine), advantageously sulphonyl chloride, and;
an organic base which simultaneously cannot be alkylated and is liposoluble;
advantageously a solvent of low polarity; and by the fact that the organic part of the said sulphonyl is perfluorinated on the carbon carried by the sulphur.

Another aim of the present invention is to provide for the use of sulphonyl chloride, perfluorinated on the carbon carried by the sulphur, that is to say adjoining it, in the mono- and bissulphonylation of ammonia, aqueous ammonia or amide, including sulphamide. And this advantageously in the presence of an organic base which cannot be alkylated and is liposoluble. And this in particular in the syntheses resulting in salts, advantageously alkaline salts, of imide carrying at least one, preferably two, sulphone groups perfluorinated on the aliphatic carbon (that is to say sp3 carbon) adjoining the sulphur.

One of the advantages of the use of the chloride is a low sensitivity to side reactions with water.

In order to better understand the invention, the following typical reactions can be given by way of indication:

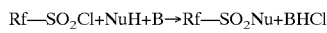

Rf—SO$_2$Cl+NuH+B→Rf—SO$_2$Nu+BHCl or

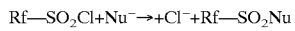

Rf—SO$_2$Cl+Nu$^-$→+Cl$^-$+Rf—SO$_2$Nu and if, as is preferred, Nu is Nu'H in nature (or, more specifically, if the nucleophilic functional group under consideration of Nu has the structure —NH— [that is to say, the structure NH$^-$ or NH$_2$])

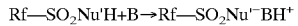

Rf—SO$_2$Nu'H+B→Rf—SO$_2$Nu'$^-$BH$^+$

NuH and Nu$^-$ respectively represent the nucleophile in the neutral and anionic form.

The most advantageous substrates are those where Nu is chosen from Ar—SO$_2$—NH—, in particular R—SO$_2$—NH—, including and preferably Rf—SO$_2$—NH—.

The following non-limiting examples illustrate the invention:

EXAMPLE 1

Preparation of Trifluoromethanesulphonamide: CF$_3$SO$_2$NH$_2$
Reaction in Anhydrous Medium:

15.3 g of trifluoromethanesulphonyl chloride, in solution in 103 g of anhydrous isopropyl ether, are charged to a reactor. The mixture is cooled to 5° C. and ammonia is slowly added over 2 h. After stirring for 5 h at 5° C., 24.8 g of water are added in order to dissolve the salts. The mixture is subsequently acidified by addition [lacuna] 20.7 g of a 36% aqueous hydrochloric acid solution.

After a further addition of 13 g of water, the phases are separated. The aqueous phase is washed with 50 g of isopropyl ether. The organic phases are combined and the solvent is removed under reduced pressure.

10.15 g of trifluoromethanesulphonamide as a white solid are thus obtained.

Melting [lacuna] (Koffler)=190° C.
Reaction in Aqueous Medium:

The reaction is carried out analogously by using a 30% aqueous ammonia solution.

EXAMPLE 2

Preparation of Lithium Bistrifluoromethylsulphinimide 1 l of monochlorobenzene and 164.6 g of trifluoromethanesuphonamide, prepared according to the preceding example, are charged to a reactor. 224.6 g of triethylamine are subsequently added to this suspension. The solution obtained is cooled to 5° C. A solution of 187 g of trifluoromethanesulphonyl chloride in 191 g of monochlorobenzene is subsequently added over 40 min at 0–5° C.

The temperature is subsequently brought to 28° C. After reacting for 4 h, the reaction mixture is filtered.

The filtrate is degassed by bubbling nitrogen and then washed with 436 g of water. The 2 lower organic phases are recovered and again washed with 507 g of water.

These organic phases are subsequently treated with a solution of 46.7 g of lithium hydroxide hydrate in 216 g of water. The mixture obtained contains two phases.

The aqueous phase is recovered and extracted with 226 g of isopropyl ether.

The latter organic phase is evaporated under reduced pressure to result in 206 g of crude lithium bistrifluoromethanesulphonimide in the form of a yellowish solid.

Yd=60%;

19F NMR=−1.8 ppm.

EXAMPLE 3

Reaction in the Presence of Diisopropylethylamine 11.2 g (0.079 M) of the amide of trifluoromethanesulphonic acid in 73 g of monochlorobenzene are charged to a reactor. After addition of 20.7 g (0.16 M) of diisopropylethylamine, 14.7 g (0.087 M) of trifluoromethanesulphonyl chloride, in solution in 15 g of monochlorobenzene, are run in at 10° C. for 45 min. The mixture is subsequently stirred for 4 h at 30° C.

The treatment is carried out as in the preceding example and results in 20.4 g of lithium bistrifluoromethanesulphonimide assaying at 98% (yd=[(20.4/303)/0.079]×0.98=83% [lacuna].

EXAMPLES 11 to 13

Role of the Solvent

To give a better demonstration of the role of the solvents, use was made of a base, the salt of which exhibits mediocre solubility:

| Example No. | Reactants | Solvent | Conditions | Results |
|---|---|---|---|---|
| 4 | CF$_3$SO$_2$NH$_2$ = 1.6 g<br>CF$_3$SO$_2$Cl = 1 eq.<br>NEt$_3$ = 2 eq. | CH$_2$Cl$_2$ | Addition CF$_3$SO$_2$Cl at 0° C.<br>Reaction 13 h at 20° C. | Conversion CF$_3$SO$_2$NH$_2$ = 80%<br>Yield = 43% |
| 5 | CF$_3$SO$_2$NH$_2$ = 3.1 g<br>CF$_3$SO$_2$Cl = 1 eq.<br>NEt$_3$ = 2 eq. | CH$_2$Cl$_2$ | Introduction CH$_2$Cl$_2$ + CF$_3$SO$_2$NH$_2$ + 1 eq. NEt$_3$<br>Addition CF$_3$SO$_2$Cl at 0° C.<br>Run in 1 eq. NEt$_3$ at 0° C.<br>Reaction 3 h at 20° C. | Conversion CF$_3$SO$_2$NH$_2$ = 76%<br>Yield = 31% |

-continued

| Example No. | Reactants | Solvent | Conditions | Results |
|---|---|---|---|---|
| 6 | $CF_3SO_2NH_2$ = 1.4 g<br>$CF_3SO_2Cl$ = 1 eq.<br>$NEt_3$ = 2 eq. | DIPE | Addition $CF_3SO_2Cl$ at 0° C.<br>Reaction 3 h at 20° C. | Conversion $CF_3SO_2NH_2$ = 80%<br>Yield = 33% |
| 7 | $CF_3SO_2NH_2$ = 1 g<br>$CF_3SO_2Cl$ = 1 eq.<br>$NEt_3$ = 2 eq. | MCB | Addition $CF_3SO_2Cl$ at 0° C.<br>Reaction 13 h at 20° C. | Quantitatively determined yield = 67% |
| 8 | $CF_3SO_2NH_2$ = 1.85 g<br>$CF_3SO_2Cl$ = 1 eq.<br>Pyridine = 2 eq. | $CH_2Cl_2$ | Addition $CF_3SO_2Cl$ at 0° C.<br>Reaction 7 h at 30° C.<br>Autogenous pressure | Conversion $CF_3SO_2NH_2$ = 35%<br>Yield = 24% |
| 9 | $CF_3SO_2NH_2$ = 1.62 g<br>$CF_3SO_2Cl$ = 1.1 eq.<br>Pyridine = 2 eq. | DIPE | Addition $CF_3SO_2Cl$ at 0° C.<br>Reaction 7 h at 30° C.<br>Autogenous pressure | Conversion $CF_3SO_2NH_2$ = 30%<br>Yield = 3% |
| 10 | $CF_3SO_2NH_2$ = 1.02 g<br>$CF_3SO_2Cl$ = 1.1 eq.<br>Pyridine = 2 eq. | MCB | Addition $CF_3SO_2Cl$ at 0° C.<br>Reaction 7 h at 30° C.<br>Autogenous pressure | Conversion $CF_3SO_2NH_2$ = 63%<br>Yield = 4% |
| 11 | $CF_3SO_2NH_2$ = 1.91 g<br>$CF_3SO_2Cl$ = 1.1 eq.<br>DIPEA = 2 eq. | $CH_2Cl_2$ | Addition $CF_3SO_2Cl$ at 0° C.<br>Reaction 7 h at 20° C. | Conversion $CF_3SO_2NH_2$ = 92%<br>Yield = 85% |
| 12 | $CF_3SO_2NH_2$ = 1.28 g<br>$CF_3SO_2Cl$ = 1.2 eq.<br>DIPEA = 2 eq. | | Addition $CF_3SO_2Cl$ at 0° C.<br>Reaction 8 h at 20° C. | Conversion $CF_3SO_2NH_2$ > 91%<br>Yield = 90% |
| 13 | $CF_3SO_2NH_2$ = 1.2 g<br>$CF_3SO_2Cl$ = 1.2 eq.<br>DIPEA = 2 eq. | MCB | Addition $CF_3SO_2Cl$ at 0° C.<br>Reaction 8 h at 20° C. | Conversion $CF_3SO_2NH_2$ > 98%<br>Yield = 97% |

DIPE: diisopropyl ether
MCB: monochlorobenzene
DIPEA: diisopropylethylamine
*The analyses of the various tests were carried out by fluorine NMR spectroscopy with internal standard.

What is claimed is:

1. A process for the preparation of perfluorosulphonamides or perfluorosulphonimides, comprising the steps of:
   1) carrying out a perfluorosulphonylation reaction by contacting a nucleophile, whose nucleophilic atom is a nitrogen atom, with a reactant comprising a sulphonyl heavy halide having an organic part, and an organic base which simultaneously cannot be alkylated and is liposoluble, said base being selected from the group consisting of a hindered dialkylphosphine, trialkylphosphine, phosphonium hydroxide, hindered dialkylamine, trialkylamine or ammonium hydroxide, the organic part of said sulphonyl heavy halide is perfluorinated on the carbon carried by the sulphur; and
   2) recovering the perfluorosulphonamides or perfluorosulphonimides thus formed.

2. A process according to claim 1, wherein the sulphonyl heavy halide is sulphonyl chloride.

3. A process according to claim 1, wherein said nucleophile is in a neutral or anionic form and has, as associated acid, an acid for which the $pK_a$ is at most equal to approximately 7.

4. A process according to claim 3, wherein the $pK_a$ is at most equal to 5.

5. A process according to claim 1, wherein said nitrogen of the nucleophile is connected to an electron-withdrawing group.

6. A process according to claim 5, wherein the electron-withdrawing group is a sulphonyl group.

7. A process according to claim 5, wherein the nucleophile is a sulphamide of a sulphonic acid wherein the sulphur is bonded to an aryl, or a sulphamide of a sulphonic acid wherein the sulphur is bonded to an aliphatic group.

8. A process according to claim 5, wherein the nucleophile is a sulphamide of a sulphonic acid wherein the sulphur is bonded to an aliphatic group and having a perfluorinated carbon adjoining the sulphur.

9. A process according to claim 5, wherein said nucleophile is a salt of a sulphonamide and of an organic base which cannot be alkylated.

10. A process according to claim 5, wherein said nucleophile is a sulphonamide in the form of a liposoluble salt with an organic base which cannot be alkylated and is liposoluble.

11. A process according to claim 1, wherein said organic base which cannot be alkylated and is liposoluble exhibits a high solubility in benzene defined as symbol "s" in the "Handbook of Chemistry and Physics", or defined as symbol "v" in the "Handbook of Chemistry and Physics".

12. A process according to claim 9, wherein said organic base which cannot be alkylated exhibits a high solubility in benzene defined as symbol "s" in the "Handbook of Chemistry and Physics", or defined as symbol "v" in the "Handbook of Chemistry and Physics".

13. A process according to claim 1, wherein the organic base which cannot be alkylated and is liposoluble is associated with an acid whose $pK_a$ is greater than or equal to that of said sulphonamide.

14. A process according to claim 9, wherein the organic base which cannot be alkylated is associated with an acid whose $pK_a$ is greater than or equal to that of said sulphonamide.

15. A process according to claim 1, wherein step 1) is carried out in an organic solvent having a miscibility of at most 10% by mass with water.

16. A process according to claim 9, wherein said nucleophile is a salt of a sulphonamide and of an organic base which cannot be alkylated, said organic base which cannot be alkylated is identical to said organic base which cannot be alkylated and is liposoluble.

17. A process according to claim 9, wherein said step 1) is carried out in an organic solvent wherein said salt is soluble therein.

18. A process according to claim 17, wherein the miscibility of the solvent with water is at most 2% by mass.

19. A process according to claim 17, wherein said salt is soluble in said solvent to a concentration level of at least 0.2M.

20. A process according to claim 1, wherein the amount of said base added during step 1) wherein hydrohalic acid is given off, is at least equal to the amount necessary to neutralise said hydrohalic acid.

21. A process according to claim 1, wherein the organic part of said sulphonyl chloride is perfluorinated on the carbon carried by the sulphur.

22. A process according to claim 7, wherein the organic part of said sulphonyl chloride is the same as the one of said sulphonamide.

23. A process according to claim 7, wherein the organic parts of said sulphonyl chloride and of said sulphonamide are alike or different, and are of formula (Rf):

$$—(CX_2)_p—EWG$$

wherein:

the X groups, which are alike or different, represent a fluorine or a radical of formula $C_nF_{2n+1}$, with n an integer at most equal to 8;

p represents an integer at most equal to 2; and

EWG represents an electron-withdrawing group, whose optional functional groups are inert under the reaction conditions, and the total carbon number of Rf is between 1 and 15.

24. A process according to claim 23, wherein EWG represents a fluorine or a perfluorinated group of formula $C_nF_{2n+1}$, with n an integer at most equal to 5, the total carbon number of Rf being between 1 and 10.

25. A process according to claim 1, wherein said nucleophile is a salt of sulphonamide, and said process further comprising:

3) treating said perfluorosulphonamides or perfluorosulphonimides with lithium hydroxide or a basic lithium salt.

* * * * *